(12) United States Patent
Jung (10) Patent No.: US 10,314,660 B2
(45) Date of Patent: Jun. 11, 2019

(54) AUTOMATED HAIR TRANSPLANT DEVICE

(71) Applicant: Yong Chul Jung, Daegu (KR)

(72) Inventor: Yong Chul Jung, Daegu (KR)

( * ) Notice: Subject to any disclaimer, the term of this patent is extended or adjusted under 35 U.S.C. 154(b) by 261 days.

(21) Appl. No.: 15/309,792

(22) PCT Filed: Apr. 20, 2015

(86) PCT No.: PCT/KR2015/003929
§ 371 (c)(1),
(2) Date: Nov. 8, 2016

(87) PCT Pub. No.: WO2015/174645
PCT Pub. Date: Nov. 19, 2015

(65) Prior Publication Data
US 2017/0143434 A1 May 25, 2017

(30) Foreign Application Priority Data

May 12, 2014 (KR) ........................ 10-2014-0056372

(51) Int. Cl.
| | |
|---|---|
| *A61B 34/30* | (2016.01) |
| *A61B 17/34* | (2006.01) |
| *A61B 17/00* | (2006.01) |
| *A61B 90/50* | (2016.01) |
| *A61B 90/00* | (2016.01) |

(52) U.S. Cl.
CPC .............. *A61B 34/30* (2016.02); *A61B 17/34* (2013.01); *A61B 17/3468* (2013.01); *A61B 90/50* (2016.02); *A61B 2017/00752* (2013.01); *A61B 2017/00969* (2013.01); *A61B 2017/3409* (2013.01); *A61B 2090/061* (2016.02); *A61B 2090/062* (2016.02)

(58) Field of Classification Search
CPC .......... A61B 2017/00752; A61B 34/30; A61B 17/34; A61B 17/3468
See application file for complete search history.

(56) References Cited

U.S. PATENT DOCUMENTS

| | | |
|---|---|---|
| 2003/0120298 A1 | 6/2003 | Gildenberg |
| 2007/0078466 A1 | 4/2007 | Bodduluri et al. |
| (Continued) | | |

FOREIGN PATENT DOCUMENTS

| | | |
|---|---|---|
| KR | 10-2000-0065685 A | 11/2000 |
| KR | 10-2008-0049793 A | 6/2008 |
| (Continued) | | |

OTHER PUBLICATIONS

International Search Report for PCT/KR2015/003929 dated Jul. 8, 2015 from Korean Intellectual Property Office.

*Primary Examiner* — Tuan V Nguyen
(74) *Attorney, Agent, or Firm* — Revolution IP, PLLC (57) ABSTRACT

Disclosed are an automated hair transplant device for transplanting a selected hair into a hair loss area, and the transplanting method comprising selecting a hair of which the root is healthy, making the selected hair have a predetermined length without harming the follicle thereof, putting the hair of a predetermined length in a hair transplant needle, inserting the hair transplant needle into the scalp into which the hair is transplanted, and then separating the hair transplant needle from the scalp while leaving the hair therein.

5 Claims, 12 Drawing Sheets

(56) References Cited

U.S. PATENT DOCUMENTS

| | | | |
|---|---|---|---|
| 2007/0078475 A1* | 4/2007 | Bodduluri | A61B 17/32053 606/187 |
| 2008/0051816 A1* | 2/2008 | Pak | A61B 17/3468 606/187 |
| 2009/0178943 A1 | 7/2009 | Oostman, Jr. et al. | |
| 2009/0198253 A1* | 8/2009 | Omori | A61B 18/18 606/130 |

FOREIGN PATENT DOCUMENTS

| | | |
|---|---|---|
| KR | 10-0958727 B1 | 5/2010 |
| KR | 10-2012-0019961 A | 3/2012 |
| WO | 2014/191827 A1 | 12/2014 |

\* cited by examiner

AUTOMATED HAIR TRANSPLANT DEVICE

CROSS REFERENCE TO PRIOR APPLICATIONS

This application is a National Stage Application of PCT International Patent Application No. PCT/KR2015/003929 filed on Apr. 20, 2015, under 35 U.S.C. § 371, which claims priority to Korean Patent Application No. 10-2014-0056372 filed on May 12, 2014, which are all hereby incorporated by reference in their entirety.

TECHNICAL FIELD

The present invention relates to an automated hair transplant device for transplanting a selected hair into a hair loss area, and more particularly, to an automated hair transplant device which allows hair transplanting work for transplanting a hair to be rapidly and accurately automated by using a method including selecting a hair of which a root is healthy, making the selected hair have a predetermined length without harming a follicle thereof, inputting the hair of the predetermined length in a hair transplant needle, inserting the hair transplant needle into a scalp into which the hair is to be transplanted, and then separating the hair transplant needle from the scalp while leaving the hair therein.

BACKGROUND ART

Conventionally, various types of hair transplant devices have been developed, but no hair transplant device capable of consecutively performing hair transplanting work exists. Therefore, there is a problem in that a doctor or person concerned with hair transplantation has to do the hair transplanting work for a long time and to undergo tremendous fatigue such that hair transplantation cannot be accurately performed when the fatigue accumulates, and accordingly, a problem in that a uniform procedure cannot be performed can occur.

Technical Problem

The present invention is directed to providing an automated hair transplant device to address the problems mentioned above.

TECHNICAL SOLUTION

The present invention has a configuration including a control device which saves information and utilizes a saved information processing technology of an advanced computer, a common precise automatic movement device, a hair transplant needle mounting unit which moves a hair transplant needle having a hair to be transplanted to a selected hair transplant area, inserts the hair transplant needle into a scalp, transplants the hair inserted into the hair transplant needle, and then pulls out the hair transplant needle such that the hair transplant needle is separated from the hair, a hair pressing pole installed at a center portion of the hair transplant needle and configured to press the hair so that the transplanted hair remains in a transplanted position thereof when the hair transplant needle is pulled out and pull out the hair transplant needle so that the hair transplant needle is separated from the hair, a hair transplant needle inserting unit which approaches the hair transplant needle mounting unit, picks up the hair transplant needle having the hair to be transplanted with electric tongs, and inserts the hair transplant needle into a needle holder of a lifting pole mounted on the hair transplant needle mounting unit, and a hair transplant needle separating unit which approaches the hair transplant needle mounting unit, picks up the hair transplant needle which outputs the hair with electric tongs, and separates the hair transplant needle from the needle holder of the lifting pole mounted on the hair transplant needle mounting unit so that operations of supplying the hair to be transplanted at a designated position, transplanting the hair to the designated position, and separating the hair transplant needle which outputs the hair from the hair transplant needle mounting unit are divided, the operations are consecutively performed at respective designated positions, and fast and precise hair transplanting work is accomplished.

Advantageous Effects

As described above, according to the present invention, hair transplantation is accomplished through preparing a hair transplant needle into which a hair, which will be transplanted and has a predetermined size, is inserted so that a follicle portion of the hair is inserted into an inner side of a hair transplant needle tip portion and by which the hair is supported so as not to be escape from the hair transplant needle, inserting the hair transplant needle at a hair transplant needle mounting unit into a hair transplant needle inserting unit, moving the hair transplant needle inserting unit to a position at which hair transplanting is performed, inserting the hair transplant needle at a designated hair transplant position, operating a hair pressing pole installed in a lifting pole, supporting the hair inserted at the inserting position by the hair pressing pole so that the hair does not relax at a hair transplant area, pulling the hair transplant needle out of a scalp while the hair is supported by the hair pressing pole, separating the needle from the hair, returning the hair pressing pole to an original position thereof, and elevating the hair transplant needle mounting unit to a movement position thereof.

Then, the hair transplant needle mounting unit which outputs the hair moves to a hair transplant needle separating unit, and when the hair transplant needle mounting unit is moved from the hair transplant area to the hair transplant needle separating unit, the hair transplant needle mounting unit at the hair transplant needle separating unit moves to the hair transplant needle inserting unit, and at the same time, the hair transplant needle mounting unit at the hair transplant needle inserting unit moves to the hair transplant area.

Then, electric tongs approaches the hair transplant needle separating unit, and the hair transplant needle which outputs the hair is separated from a needle holder of a lower end of the lifting pole, and at the hair transplant needle inserting unit, the electric tongs picks up a hair transplant needle having a hair to be transplanted and couples the hair transplant needle to the needle holder of the lower end of the lifting pole. When the hair transplant needle mounting unit moves to a hair transplant position, hair transplantation is performed at the position, the hair transplant needle which outputs the hair is separated from the hair transplant needle separating unit after the hair transplantation, the hair transplant needle mounting unit from which the hair transplant needle is separated receives a hair to be transplanted from the hair transplant needle inserting unit and moves to the hair transplant area, and the hair transplanting work can be consecutively performed. When these operations are repeatedly performed, hair transplantation is consecutively performed in the hair transplant positions, that is, a fast and efficient hair transplant can be performed.

Meanwhile, in the hair transplant needle mounting unit, the lifting pole driven by a first servo motor is installed and the needle holder is formed at the lower end of the lifting pole, and when the needle holder is inserted therein, a fastener fastened by a spring holds and supports the needle holder, a lifting operation is performed by the first servo motor within a range in which a lifting distance is calculated, a hair pressing pole is installed in the lifting pole, and the lifting operation is performed by a second servo motor. Therefore, when the hair transplant needle is inserted into the scalp, the hair pressing pole presses the hair input therein and maintains the hair at the hair transplant position, and when the hair transplant needle is raised, the hair pressing pole presses the hair such that only the hair transplant needle is raised, therefore the hair and the hair transplant needle are separated from each other, and after the hair transplant needle is output from a surface of the scalp, the hair pressing pole is raised to the original position thereof, and a hair transplantation operations are completed. This series of operations may be performed without error according to the division of operations of the lifting pole and the hair pressing pole.

Then, when the hair transplant needle mounting unit on which the hair transplant needle which output the hair is mounted reaches the hair transplant needle separating unit, electric tongs mounted at that position approaches and picks up the hair transplant needle to pull the hair transplant needle out of the needle holder. Proceeding to the next step, the hair is received and the electric tongs mounted on the hair transplant needle inserting unit picks up a hair transplant needle which is on standby and inserts the hair transplant needle into the needle holder of the lower end of the lifting pole of the hair transplant needle mounting unit, and the hair transplant needle is moved to the hair transplant area. Three operations of the hair transplantation, the needle separation, and the needle insertion are simultaneously accomplished at respective positions thereof, and therefore consecutive hair transplantation in which hairs are consecutively transplanted can be performed in the hair transplant area.

Meanwhile, the hair transplant needle mounting unit of the present invention may include one or a plurality of lifting poles, and the needle holder and the hair pressing pole can be included for every lifting pole. Therefore, one or a plurality of hairs can be transplanted to the hair transplant area at one time, and hair transplantation can be performed with a predetermined gradient, and a shape of the hair transplantation can be a linear shape, a curved shape, or an irregular shape so that naturalness can be achieved while the hair grows.

Accordingly, the present invention has advantages in that efficiency of hair transplanting work can be achieved, a work fatigue of a doctor or a person concerned with hair transplantation can be decreased, and hair transplant failure due to fatigue can be maximally prevented.

MODE FOR INVENTION

The present invention is related to an automated hair transplant device including a computer control device C configured to program, save, and output work information required for hair transplanting work, a multi-movement device 2 supported by a control plate 1, controlled by the computer control device C, and configured to move in horizontal or vertical directions by a common precise automatic movement device technology, three mounting devices 3, 3a, and 3b radially installed every 120° along an outer circumference of a lower end fixing unit 2a of the multi-movement device 2, a rotating plate 30 coupled to a lower end of a first mounting device 3 among the three mounting devices 3, 3a, and 3b, wherein the first mounting device 3 is position under a center portion, a locomotion rod 31 radially installed every 120° along and protruding from an outer circumference of the rotating plate 30 and intermittently rotated by the computer control device C, a pivot joint 31a coupled to a front end of the locomotion rod 31, a lifting pole 5 coupled to the pivot joint 31a so that an angle thereof is adjusted, provide with a vertical guiding hole 32a formed in a hair transplant needle mounting unit 32 so that the lifting pole 5 is guided by the vertical guiding hole 32a, and forcibly raised or lowered in a vertical direction by a first servo motor 4, a needle holder 6 coupled to a lower end of the lifting pole 5 and including a fastener 6a extending toward a center thereof by elasticity of a spring 6b, wherein a hair transplant needle inserted into a center portion of the fastener 6a is supported by the fastener 6a, a hair pressing pole 8 which is installed in a center hole 5a of the lifting pole 5 to be raised or lowered along the center hole 5a and whose upper end portion is coupled to a second servo motor 7 to be forcibly raised or lowered, the hair transplant needle mounting unit 32 including a hair transplant position sensor 9 mounted on the lifting pole 5 and configured to sense a position at which hair transplanting is performed using a common position sensing technology and then stop a hair transplant needle 11 at the hair transplanting position, a lifting mounting unit 3c coupled to a second mounting device 3a which is fixed to and protrudes from the lower end fixing unit 2a of the multi-movement device 2, a lifting-type supporting rod 301 mounted on the lifting mounting unit 3c, a hair transplant needle inserting unit A configured to insert the hair transplant needle 11 having a hair into the needle holder 6 of the hair transplant needle mounting unit 32 by electric tongs 302 which are mounted on the lifting-type supporting rod such that a length thereof is adjusted, a lifting mounting unit 3d coupled to a third mounting device 3b which is fixed to and protrudes from the lower end fixing unit 2a of the multi-movement device 2, a lifting-type supporting rod 301 mounted on the lifting mounting unit 3d, a hair transplant needle separating unit B configured to forcibly separate the hair transplant needle 11 supported by the needle holder 6 of the lower end of the lifting pole 5 of the hair transplant needle mounting unit 32 by electric tongs 302 which are mounted on the lifting-type supporting rod 301 such that a length thereof is adjusted, and the hair transplant needle 11 having a tubular body of which a lower end is open, a tip portion 11a is formed at an end portion of the open portion so that a follicle 10a of a hair 10 which is to be transplanted is inserted into an inner side of the tip portion 11a, and an upper end is detachably coupled to an inside of the needle holder 6 of the lifting pole 5.

In the above, the vertical guiding hole 32a installed in the hair transplant needle mounting unit 32 is formed as one or a plurality of vertical guiding holes, and the lifting pole 5 is mounted at each of the vertical guiding holes 32a, the needle holder 6 is mounted at the lower end thereof, and the hair pressing pole 8 is included in the center hole 5a of the lifting pole 5 at each of the center holes of the lifting poles 5 so that one or a plurality of hair transplants are simultaneously performed, and the hair transplant is diagonally performed with an appropriate tilt angle such that a protrusion angle of a hair is suitable with respect to a hair transplanting area, and a shape of the hair transplant is configured to have various shapes including a linear shape in which hairs are transplanted along a straight line, a curved shape in which hairs are transplanted along a curved line, and an irregular array shape in which hairs are transplanted irregularly in the hair transplanting area.

Figure 1:
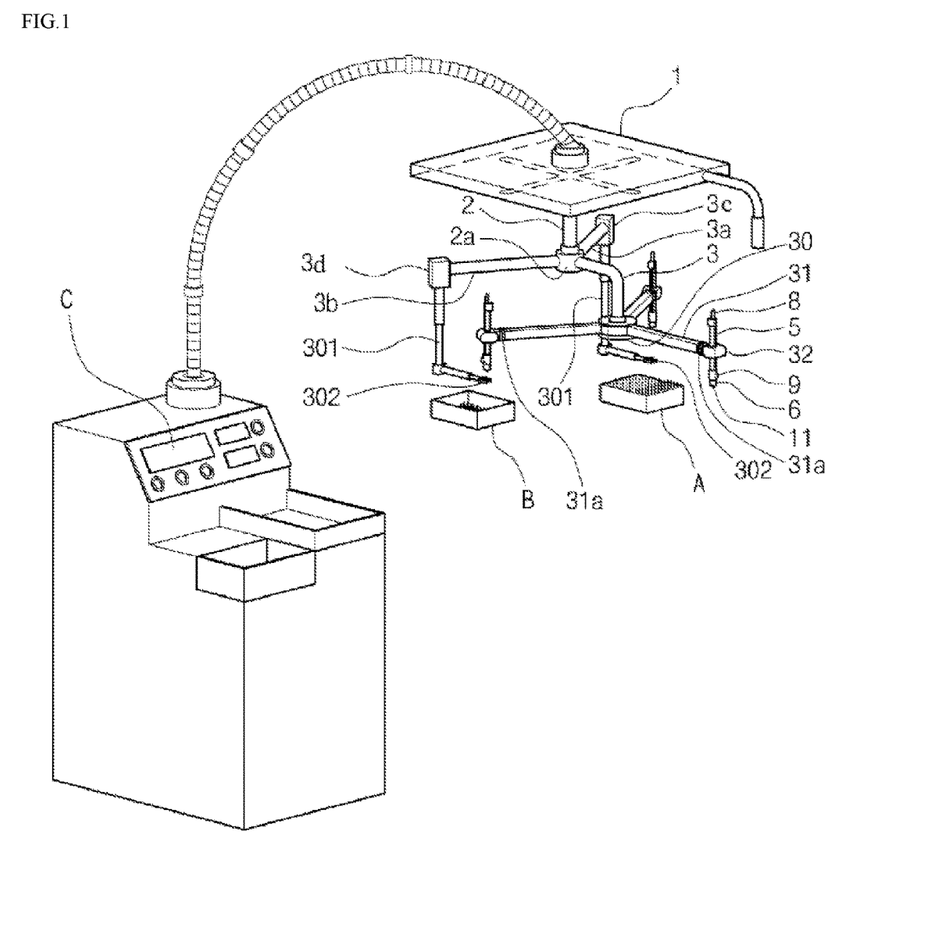
FIG. 1 is an exemplary diagram illustrating an overall structure of the present invention.
Figure 2A:
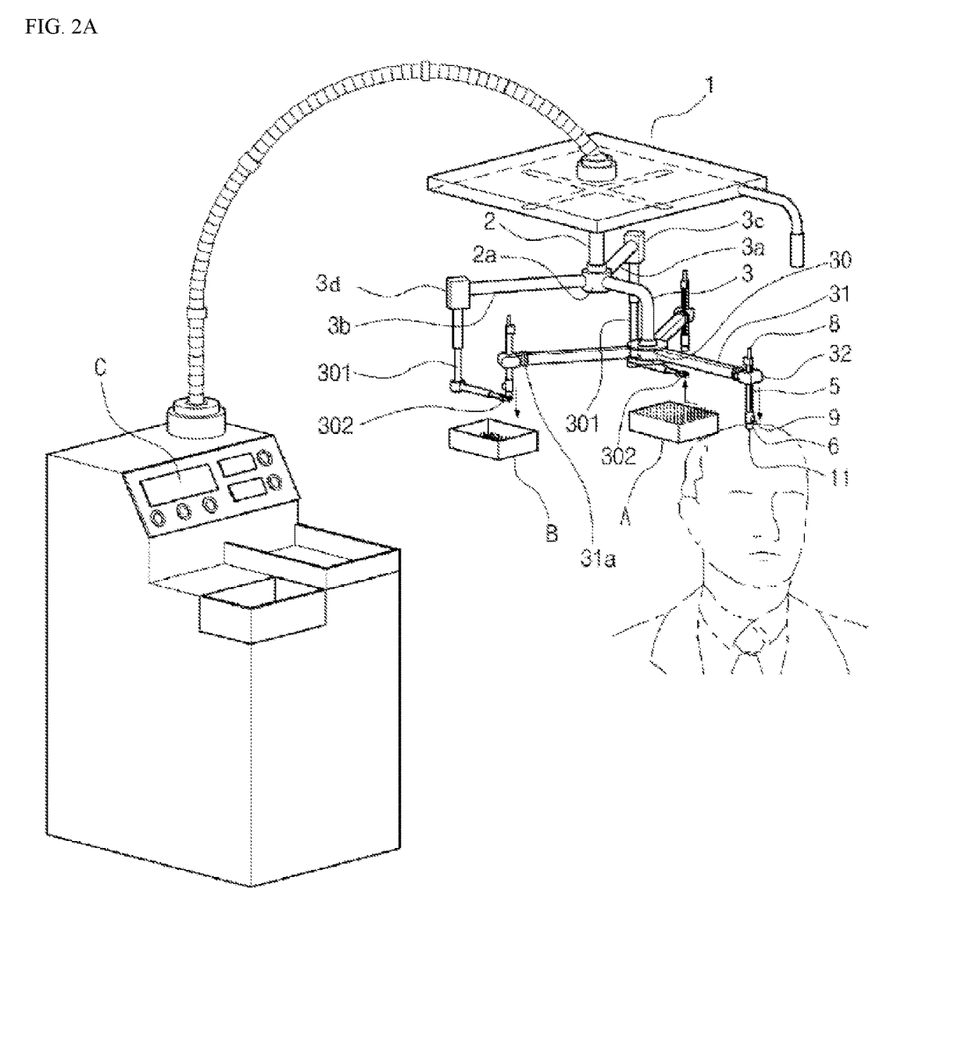
FIGS. 2A, 2B, and 2C are exemplary diagrams illustrating operational states of a hair transplant needle mounting unit of the present invention.
Figure 2B:
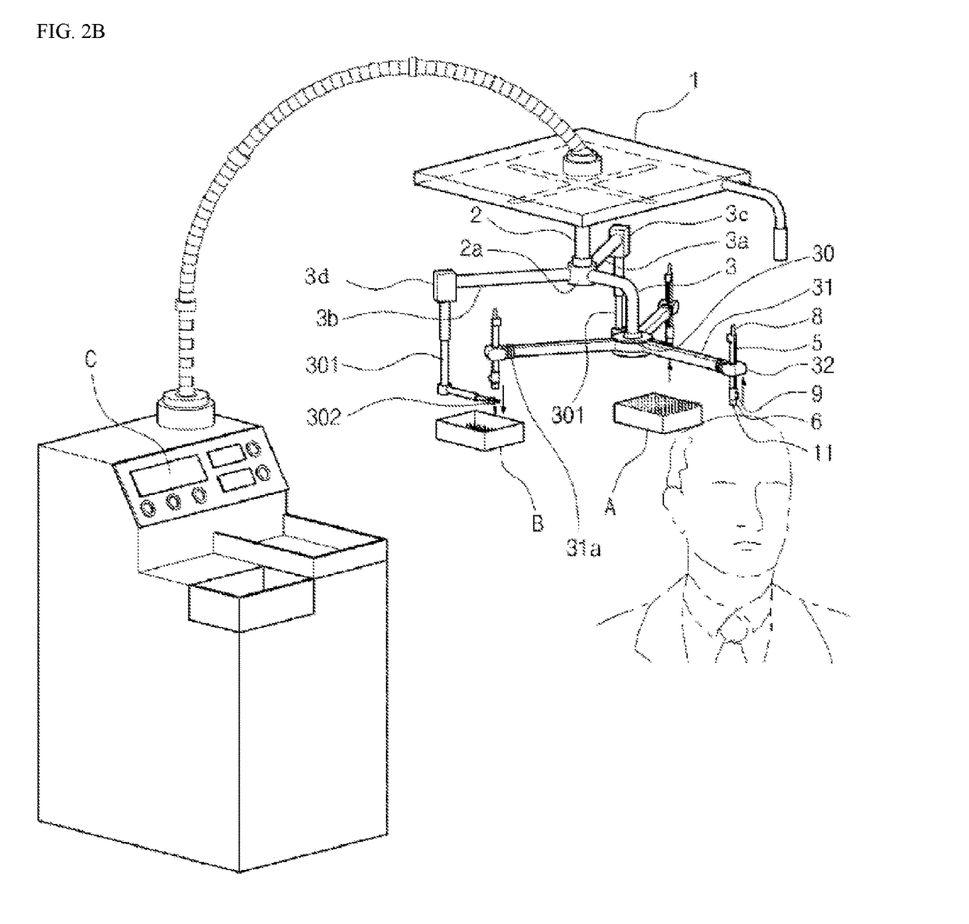
Figure 2C:
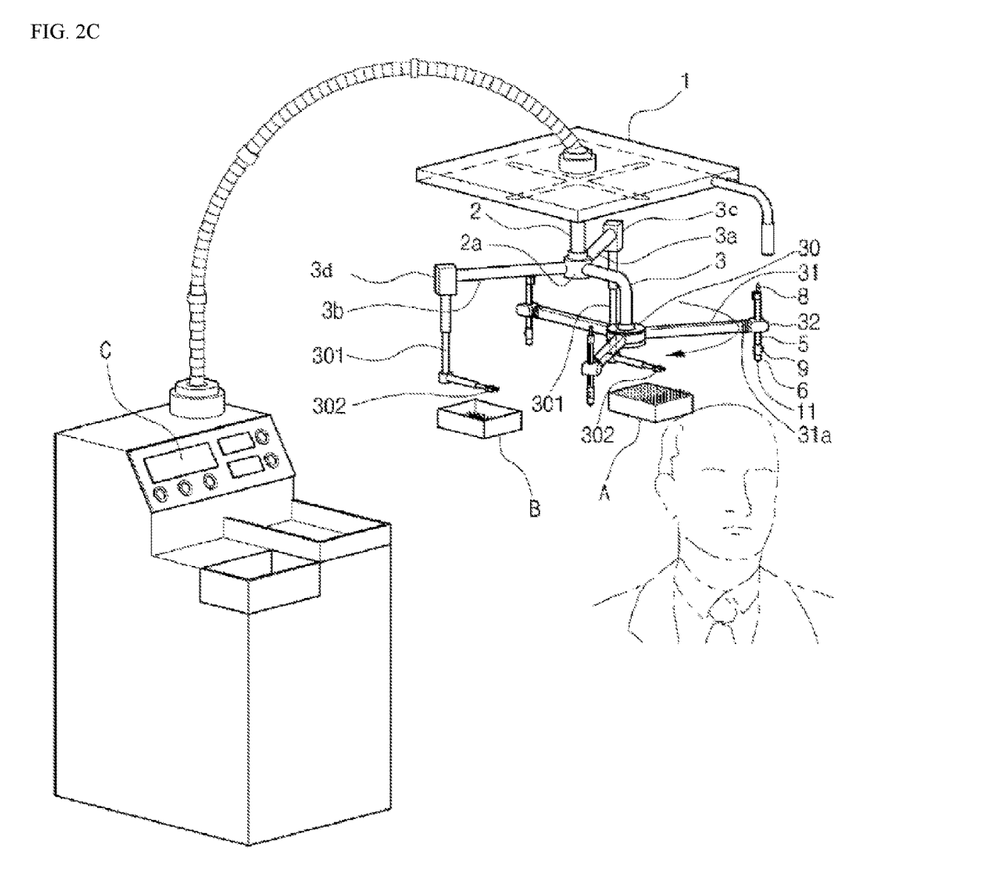
Figure 3:
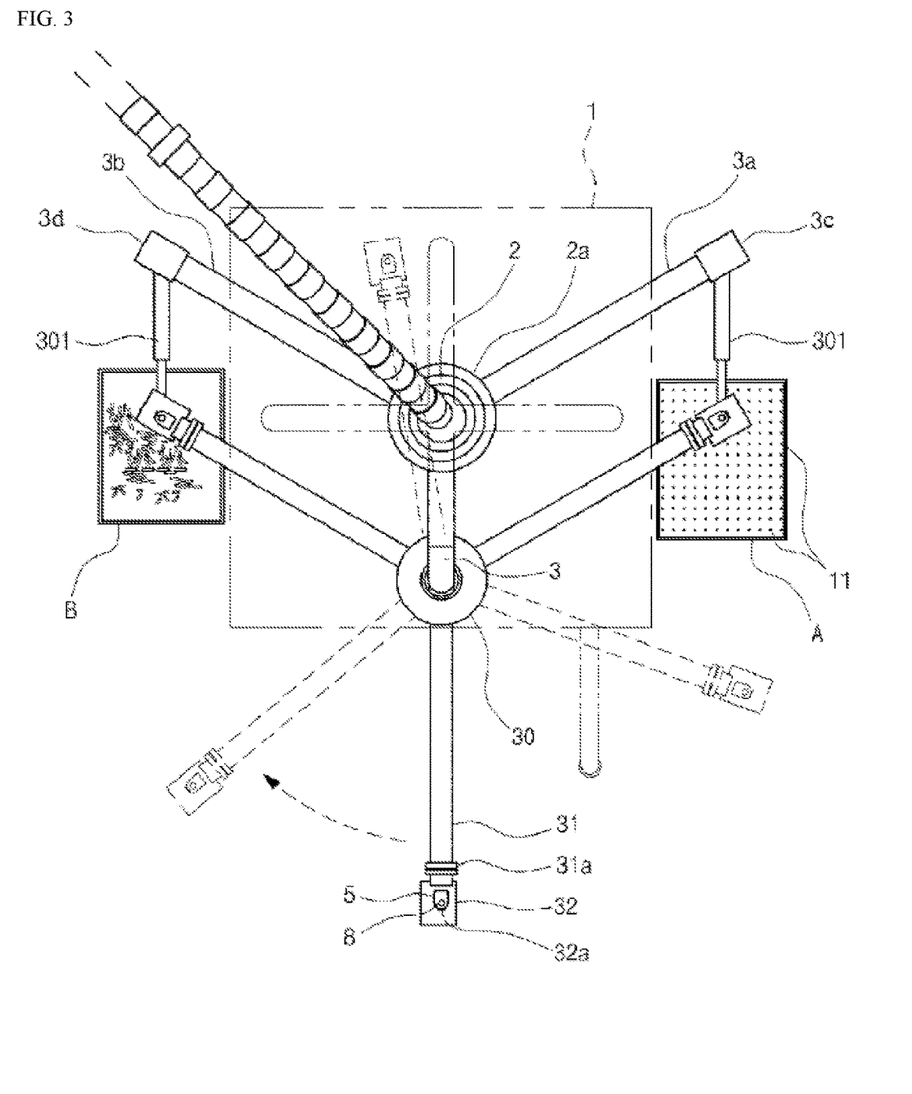
FIG. 3 is a plan view of FIG. 2.
Figure 4:
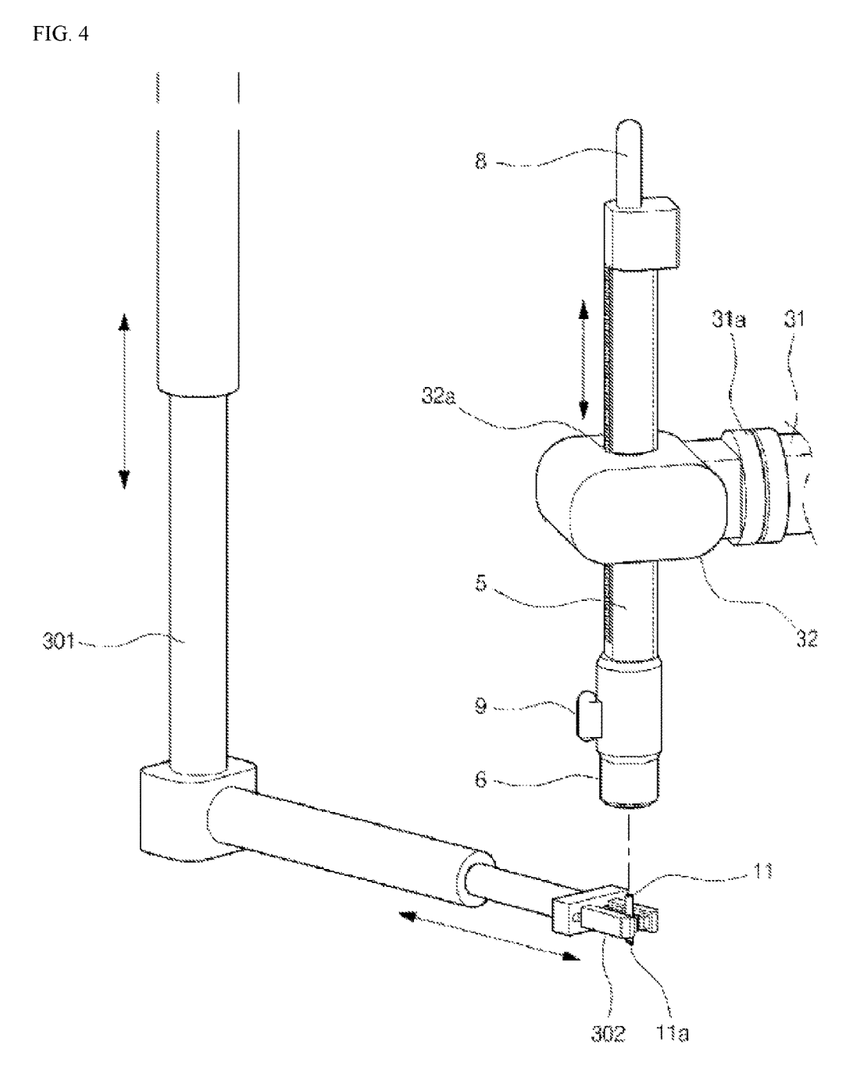
FIG. 4 is a partial enlarged view of the hair transplant needle mounting unit.
Figure 5A:
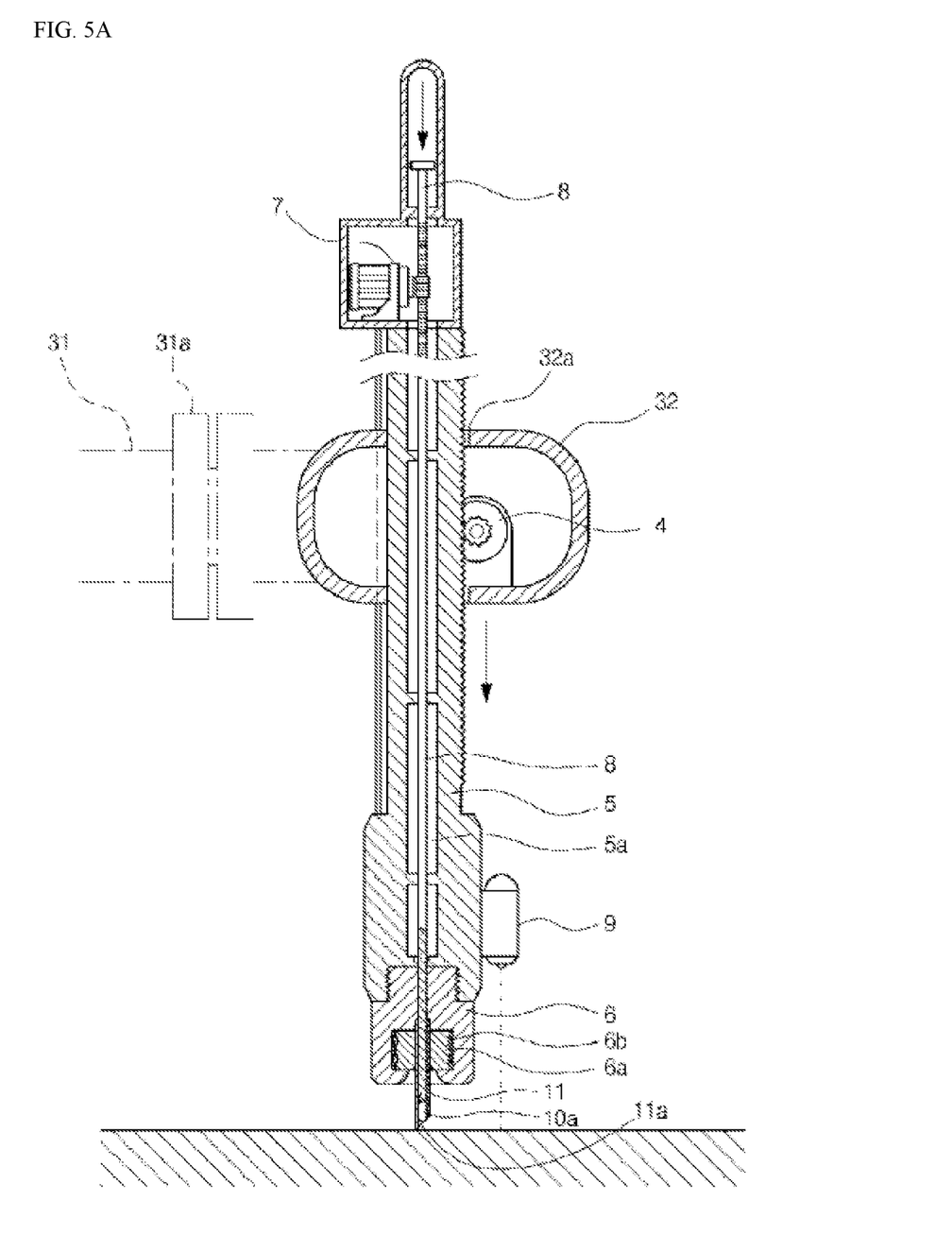
FIGS. 5A, 5B, 5C and 5D are exemplary cross-sectional views illustrating hair transplantation steps.
Figure 5B:
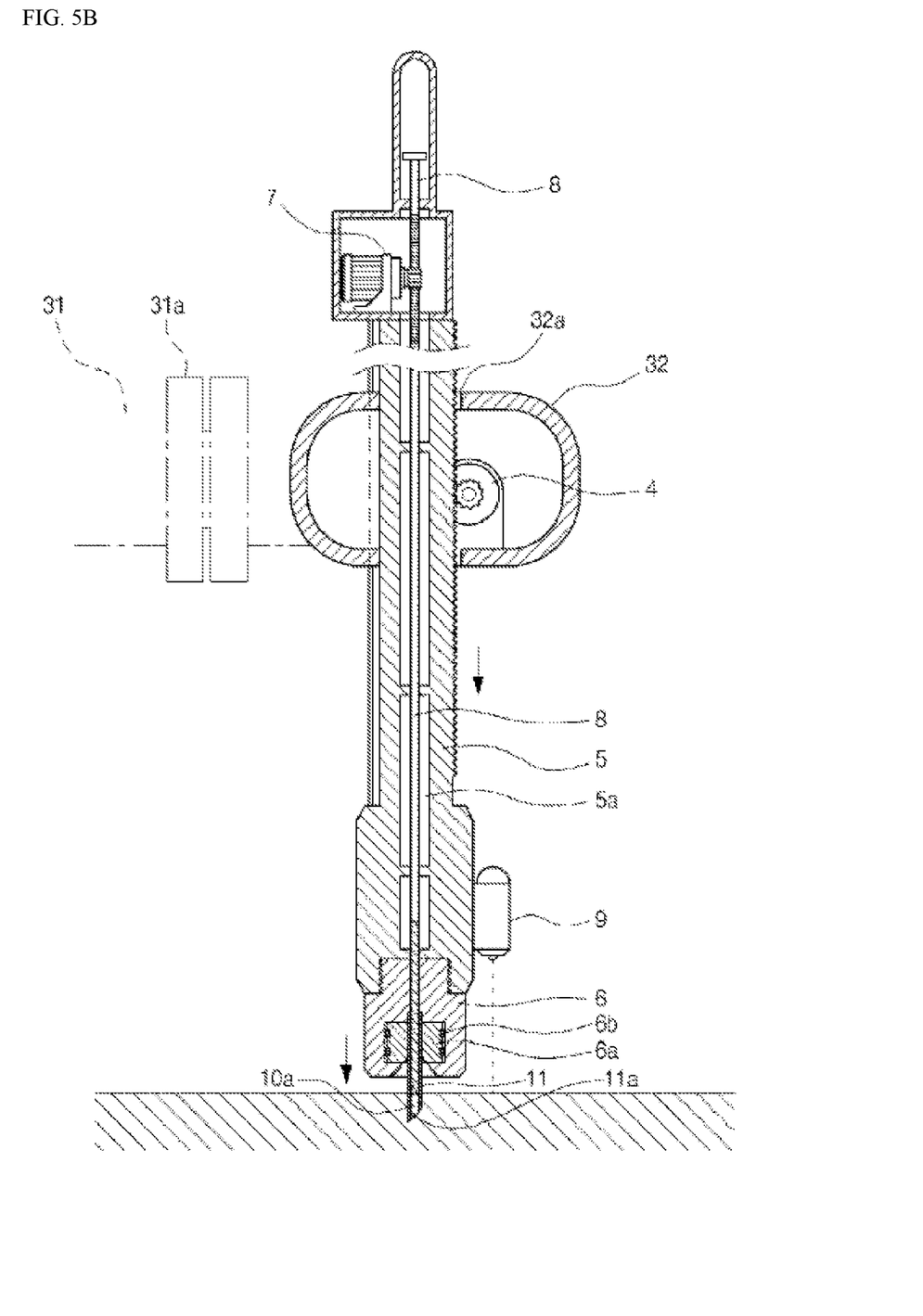
Figure 5C:
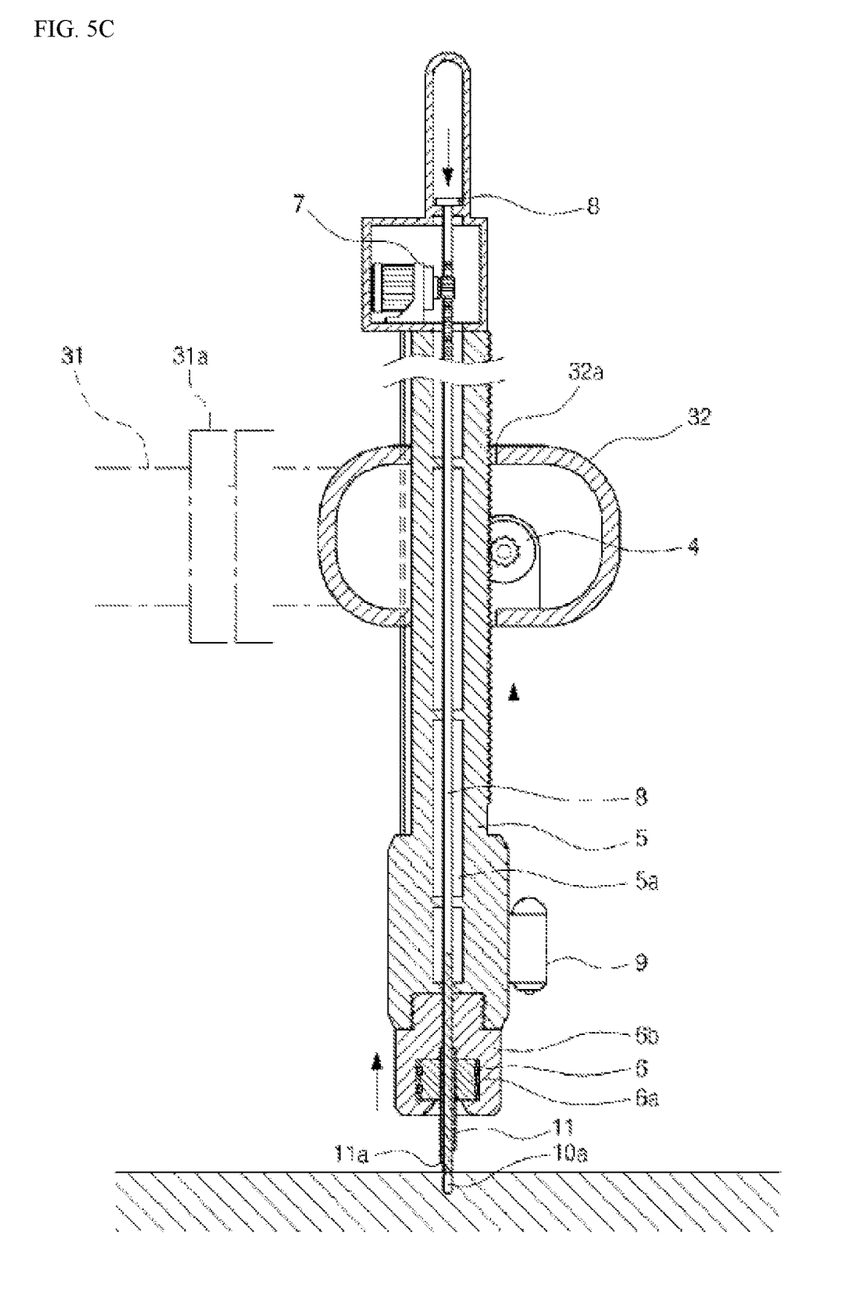
Figure 5D:
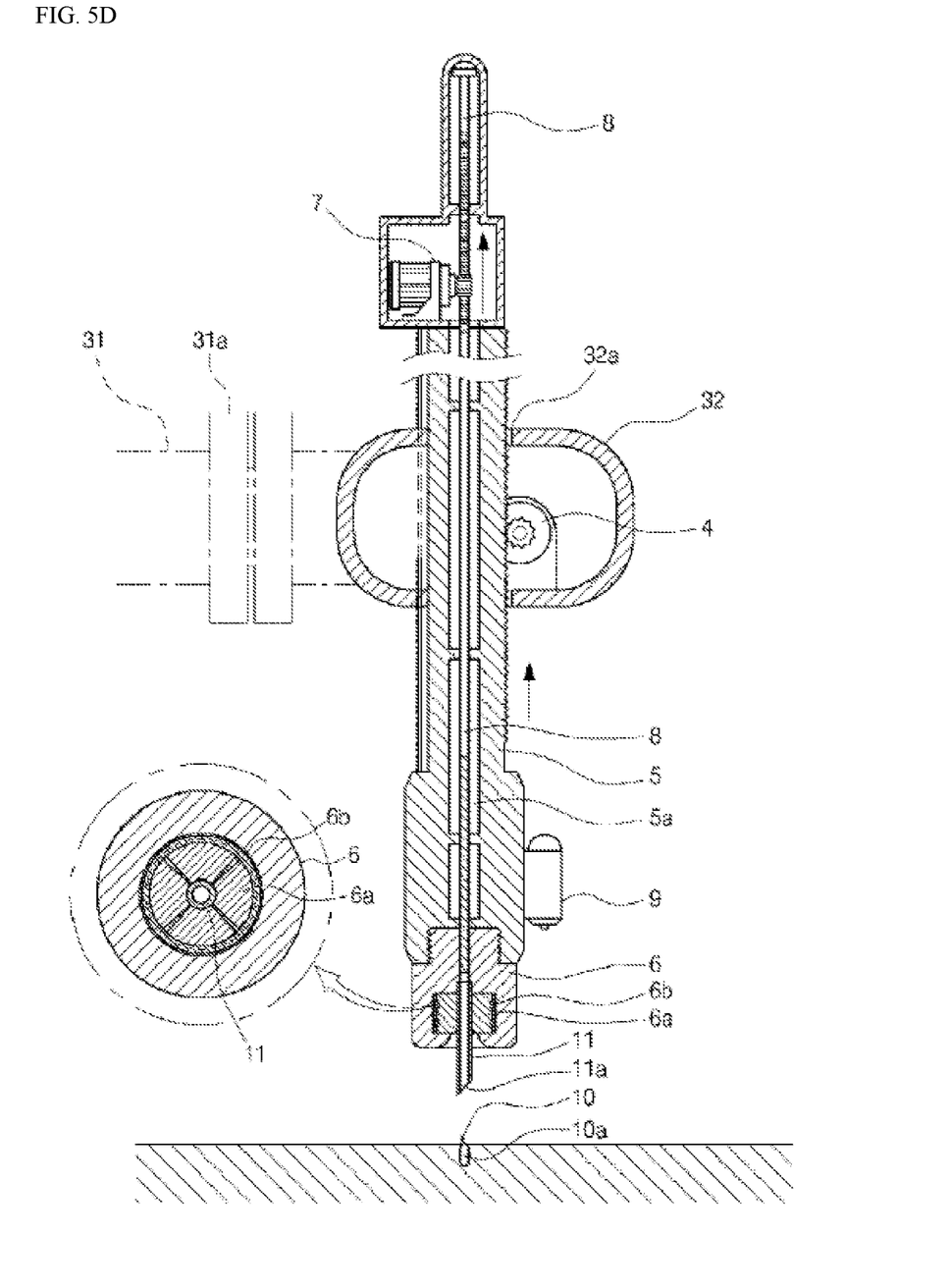
Figure 6:
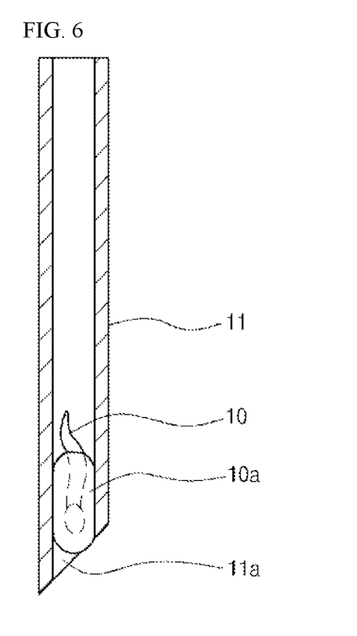
FIG. 6 is an exemplary diagram illustrating a hair transplant needle into which a hair is inserted.
Figure 7:
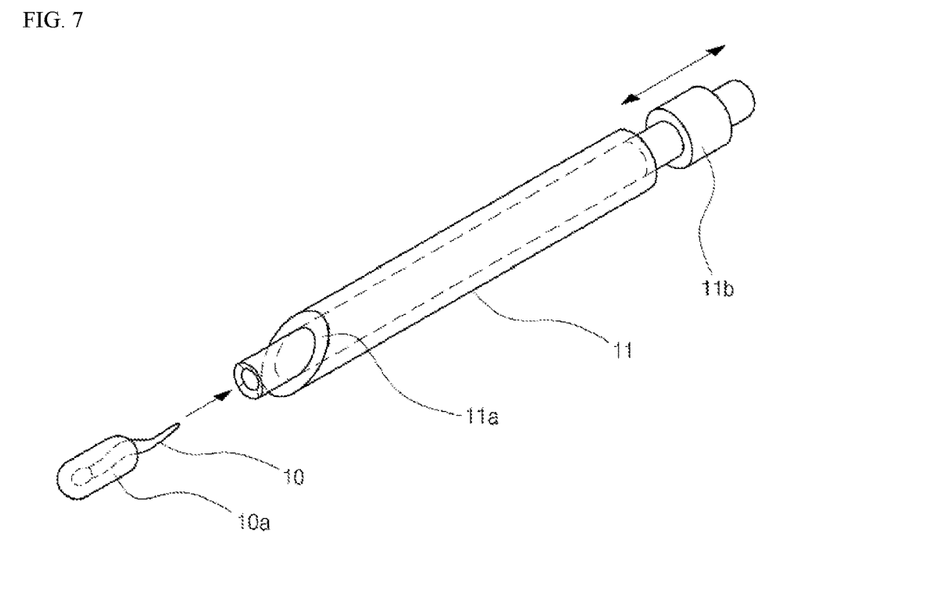
FIG. 7 is an exemplary diagram illustrating a process of inserting a hair into a hair transplant needle.
Figure 8:
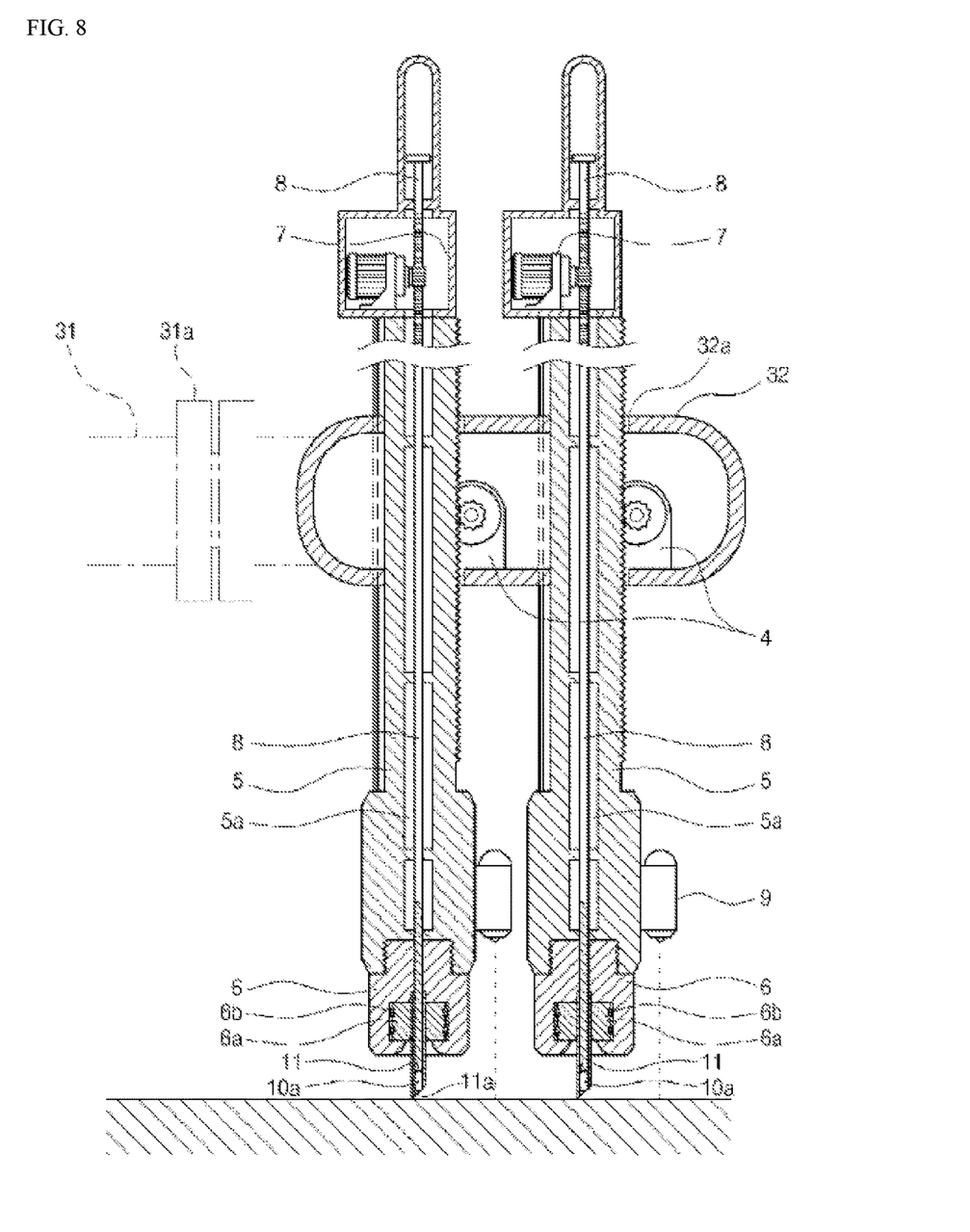
FIG. 8 is an exemplary cross-sectional view illustrating a device including a plurality of hair transplant needles.

In addition, as shown in FIG. 7, a method of the present invention for inserting the hair 10 to be transplanted in a tubular body of the hair transplant needle 11, includes inserting a tool 11b such as an absorber or tongs into the hair transplant needle 11 and holding an end of the hair 10 to be transplanted to pull and input the hair 10 into the needle so that the follicle 10a portion of the hair 10 positions at the tip portion 11a of the hair transplant needle. Therefore, a hair is received in the hair transplant needle and the hair transplant needle is inserted in the hair transplant needle mounting unit 32.

DESCRIPTION OF THE SYMBOLS

1: control plate
2: multi-movement device
2a: lower end fixing unit
3, 3a, 3b: mounting device
4: first servo motor
5: lifting pole
5a: center hole
6: needle holder
6b: spring
7: second servo motor
8: hair pressing pole
9: hair transplant position sensor
10: hair
10a: follicle
11: hair transplant needle
11a: tip portion
11b: tool
30: rotation plate
31: locomotor rod
31a: pivot joint
32: hair transplant needle mounting unit
301: lifting-type supporting rod
302: a pair of electric tongs
3c, 3d: lifting mounting unit
A: hair transplant needle inserting unit
B: hair transplant needle separating unit
C: computer

The invention claimed is:

1. An automated hair transplant device comprising:
a computer control device configured to program, save, and output work information required for hair transplanting work;
a multi-movement device supported by a control plate, controlled by the computer control device, and configured to move in a horizontal direction or a vertical direction;
a first, a second and a third mounting devices radially installed on an outer circumference of a lower end fixing unit of the multi-movement device;
a rotating plate coupled to a lower end of the first mounting device;
a plurality of locomotion rods radially installed on an outer circumference of the rotating plate and rotated by the computer control device;
a pivot joint coupled to a front end of each of the locomotion rods;
an lifting pole inserted in a vertical guiding hole formed in a hair transplant needle mounting unit, and raised or lowered in a vertical direction by a first servo motor in the hair transplant needle mounting unit;
a needle holder coupled to a lower end of the lifting pole and including a fastener extending toward a center thereof by elasticity of a spring, wherein a hair transplant needle inserted into a center portion of the fastener is supported by the fastener;
a hair pressing pole raised or lowered along a center hole of the lifting pole by using a second servo motor in the lifting pole;
a hair transplant position sensor mounted on the lifting pole and configured to sense a position at which hair transplanting is to be performed;
a first lifting mounting unit coupled to the second mounting device;
a first lifting-type supporting rod mounted on the first lifting mounting unit;
a first electric tongs mounted on the first lifting-type supporting rod such that a length thereof is adjusted and configured to insert the hair transplant needle having a hair into the needle holder;
a second lifting mounting unit coupled to a third mounting device;
a second lifting-type supporting rod mounted on the second lifting mounting unit;
a second electric tongs mounted on the second lifting-type supporting rod such that a length thereof is adjusted and configured to separate the hair transplant needle from the needle holder; and
a hair transplant needle having a tip portion formed at an end portion of the hair transplant needle so that a follicle of a hair which is to be transplanted is inserted into an inner side of the tip portion, and an upper end of the hair transplant needle detachably coupled to an inside of the needle holder of the lifting pole.

2. The automated hair transplant device of claim 1, wherein the vertical guiding hole installed in the hair transplant needle mounting unit is formed as one or a plurality of vertical guiding holes, and the lifting pole is mounted at each of the vertical guiding holes, the needle holder is mounted at the lower end thereof, and the hair pressing pole is included in the center hole of the lifting pole at each of the center holes of the lifting pole such that one or a plurality of hair transplants are performed.

3. The automated hair transplant device of claim 1, wherein a shape of the hair transplant is configured to have at least one of a linear shape, a curved shape, and an irregular array shape.

4. The automated hair transplant device of claim 1, wherein if the hair transplanting is performed by using the hair transplant needle, the second electric tongs separates the hair transplant needle from the needle holder and the first electric tongs inserts a new hair transplant needle having a hair into the needle holder.

5. The automated hair transplant device of claim 4, wherein the hair transplant needle mounting unit, the second electric tongs and the first electric tongs operate repeatedly according to rotation of the locomotion rods.

\* \* \* \* \*